(12) United States Patent
Ishii et al.

(10) Patent No.: US 9,060,958 B2
(45) Date of Patent: Jun. 23, 2015

(54) TYROSINASE INHIBITOR PRODUCED USING DRIED EARTHWORM POWDER, AND METHOD FOR PRODUCING SAME

(75) Inventors: Yoichi Ishii, Miyazaki (JP); Kazuyuki Ishii, Miyazaki (JP)

(73) Assignee: WELL STONE CO., Miyazaki (JP)

( * ) Notice: Subject to any disclaimer, the term of this patent is extended or adjusted under 35 U.S.C. 154(b) by 0 days.

(21) Appl. No.: 14/235,191

(22) PCT Filed: Jul. 24, 2012

(86) PCT No.: PCT/JP2012/068718
§ 371 (c)(1),
(2), (4) Date: Jan. 27, 2014

(87) PCT Pub. No.: WO2013/018587
PCT Pub. Date: Feb. 7, 2013

(65) Prior Publication Data
US 2014/0154331 A1    Jun. 5, 2014

(30) Foreign Application Priority Data
Jul. 29, 2011 (JP) .................................. 2011-167720

(51) Int. Cl.
| | | |
|---|---|---|
| *A61K 36/62* | (2006.01) | |
| *A61K 8/98* | (2006.01) | |
| *A61Q 19/02* | (2006.01) | |
| *A61Q 19/00* | (2006.01) | |
| *A61K 8/02* | (2006.01) | |
| *A61K 35/62* | (2006.01) | |

(52) U.S. Cl.
CPC . *A61K 8/98* (2013.01); *A61Q 19/02* (2013.01); *A61Q 19/00* (2013.01); *A61K 8/987* (2013.01); *A61K 8/022* (2013.01); *A61K 35/62* (2013.01)

(58) Field of Classification Search
USPC .................................................. 424/537, 520
IPC ....................................................... A61K 35/62
See application file for complete search history.

(56) References Cited

U.S. PATENT DOCUMENTS

| | | | | |
|---|---|---|---|---|
| 4,568,545 | A * | 2/1986 | Mihara et al. | 424/94.64 |
| 5,186,944 | A * | 2/1993 | Ishii et al. | 424/520 |
| 5,576,026 | A * | 11/1996 | Charter et al. | 424/520 |
| 8,137,701 | B2 * | 3/2012 | Ishii et al. | 424/520 |
| 8,394,417 | B2 * | 3/2013 | Ishii et al. | 424/520 |
| 2008/0206352 | A1 * | 8/2008 | Li | 424/520 |
| 2009/0238891 | A1 * | 9/2009 | Ishii et al. | 424/520 |
| 2010/0074962 | A1 * | 3/2010 | Aiken et al. | 424/520 |
| 2011/0086106 | A1 * | 4/2011 | Ishii et al. | 424/520 |
| 2012/0294950 | A1 | 11/2012 | Ishii | |

FOREIGN PATENT DOCUMENTS

| | | |
|---|---|---|
| CA | 2 747 770 | 7/2010 |
| CN | 1657098 | 8/2005 |
| JP | 63-238009 | 10/1988 |
| JP | 2007-39404 | 2/2007 |
| JP | 2009/249362 | * 10/2009 |
| JP | 2009-249362 | 10/2009 |
| JP | 2011-32173 | 2/2011 |
| JP | 2011-37764 | 2/2011 |
| WO | 2012/073593 | 6/2012 |

OTHER PUBLICATIONS

International Search Report issued Oct. 23, 2012 in International (PCT) Application No. PCT/JP2012/068718.
Office Action issued Jul. 1, 2014 in corresponding Russian Application No. 2014107467/15, with English language translation thereof.

* cited by examiner

*Primary Examiner* — Chris R Tate
(74) *Attorney, Agent, or Firm* — Wenderoth, Lind & Ponack, L.L.P.

(57) ABSTRACT

The present invention provides a highly safe tyrosinase inhibitor having excellent tyrosinase-inhibiting action, and a method for producing the tyrosinase inhibitor. The method for producing a tyrosinase inhibitor comprises the steps of contacting a live earthworm with hydroxycarboxylic acid powder, diluting the resulting mixture with water to adjust the pH to 2 to 5, and then leaving the resulting dilution to stand for 3 to 180 minutes, or contacting a live earthworm with an aqueous solution of hydroxycarboxylic acid having a pH of 2 to 5 and then leaving the resulting mixture to stand for 3 to 180 minutes; followed by washing the live earthworm with water, grinding the washed earthworm, and then freeze-drying the obtained ground product.

4 Claims, 4 Drawing Sheets

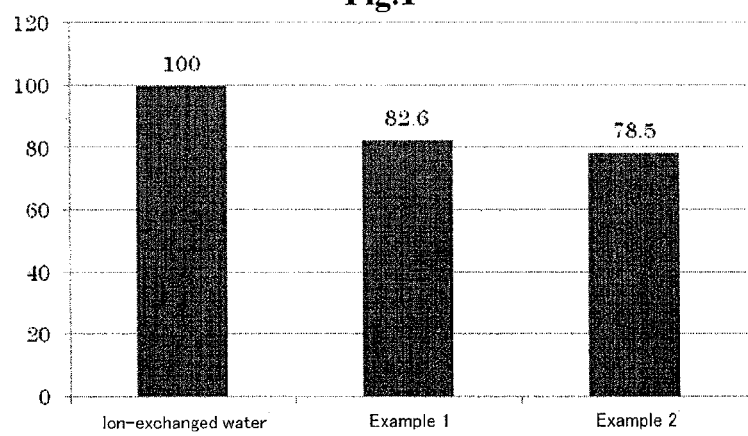
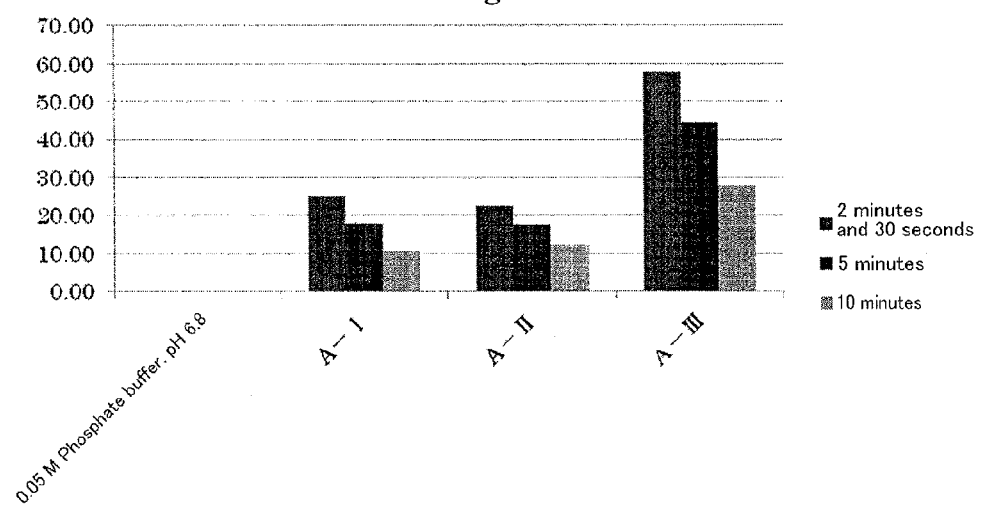

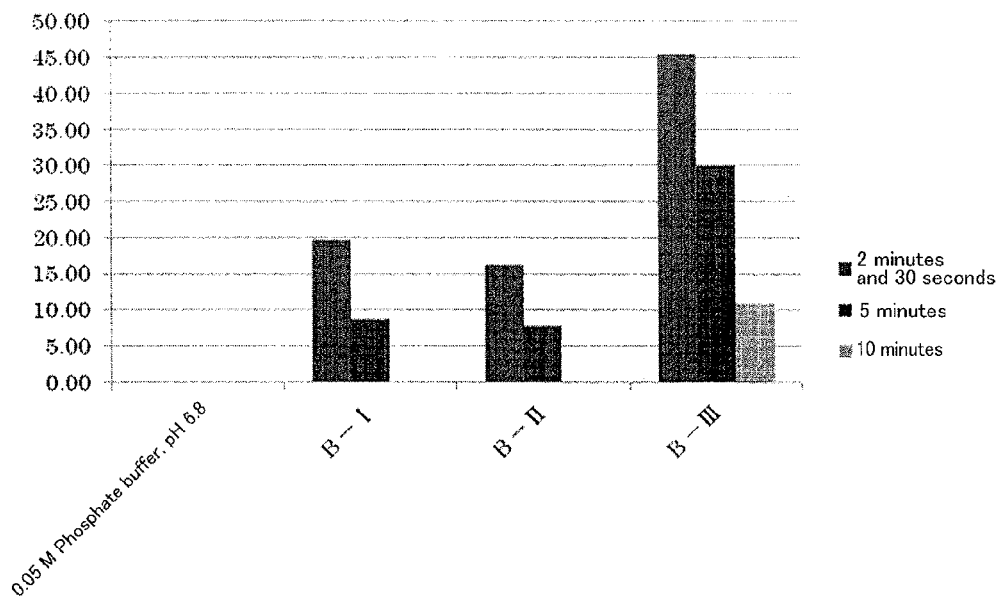
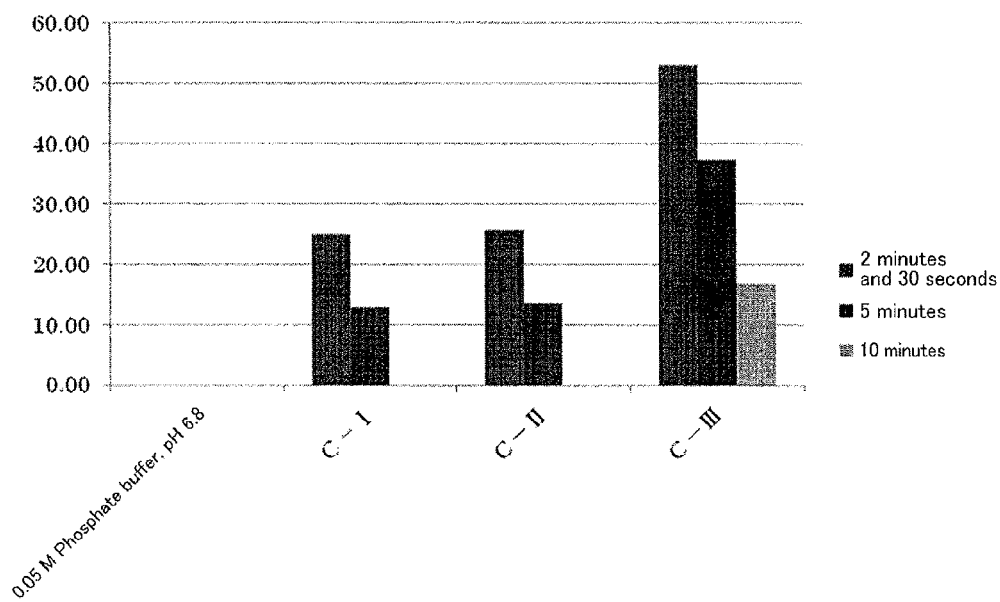

TYROSINASE INHIBITOR PRODUCED USING DRIED EARTHWORM POWDER, AND METHOD FOR PRODUCING SAME

TECHNICAL FIELD

The present invention relates to a tyrosinase inhibitor produced using dry earthworm powder, and a method for producing the tyrosinase inhibitor. More specifically, the present invention relates to a safe and highly effective tyrosinase inhibitor produced using dry earthworm powder, and a method for producing the tyrosinase inhibitor.

BACKGROUND ART

While anti-aging products have been increasingly demanded due to the recent progress of aging of the society, young people have remarkably increasing interest in the beauty of their skin itself. Thus, the importance of cosmetics, especially those for skin whitening, is increasing.

Internal factors such as aging, and external factors such as ultraviolet and active oxygen cause deterioration of various functions of the skin that have been originally maintained, leading to appearance of various troubles. An example of the skin troubles is pigmentation of the skin, which appears due to spots, freckles, sunburn and the like. It is said that the main cause of pigmentation is production of the melanin precursor by enzymatic reaction of tyrosine present in the skin, followed by production of melanin by oxidation.

Substances that suppress production of melanin can be roughly divided into two types. One of these is the type that directly suppresses the activity itself of tyrosinase enzyme that influences melanin production, and the other is the type that does not directly suppress the tyrosinase activity but suppresses melanin production in pigment cells. There are also substances having both actions. Examples of generally known components that have melanin-production-suppressing action and are effective for prevention or amelioration of pigmentation include ascorbic acid, glutathione and hydroquinone, as well as other various natural plant-derived components proposed so far (e.g., Patent Documents 1 and 2).

On the other hand, earthworm extracts and dry earthworm powders have been used from ancient times in mainly oriental countries as prophylactic agents and therapeutic agents for various diseases, and examples of their uses so far known include uses as bladder-stone-reducing agents and bladder-stone-excretion-promoting agents, therapeutic agents for icterus, oxytocics, tonics, hair-growing agents, aphrodisiacs, antipyretics, therapeutic agents for convulsion, blood circulation promoters, therapeutic agents for hemiplegia, indirect analgesics, diuretics, therapeutic agents for bronchial asthma and therapeutic agents for hypertension.

Patent Document 3 discloses that earthworm extracts obtained by hydrothermal treatment followed by extraction with an organic solvent or by hydrolytic extraction have an action to suppress the tyrosinase activity.

RELATED ART DOCUMENTS

Patent Documents

[Patent Document 1] Japanese Unexamined Patent Application Publication No. 2011-032173
[Patent Document 2] Japanese Unexamined Patent Application Publication No. 2011-037764
[Patent Document 3] Japanese Unexamined Patent Application Publication No. S63-238009

SUMMARY OF THE INVENTION

Problems to be Solved by the Invention

However, among the substances that suppress melanin production, ascorbic acids are problematic in their stability. They are unstable in aqueous systems, and may cause color changes or smell changes. Thiol compounds such as glutathione have problems, for example, that they have bad smells and are easily oxidized. Further, hydroquinone has a problem of safety to the skin.

Further, among the earthworm extracts described in the above Patent Document 3, those produced by heating and mincing earthworms followed by extraction with an organic solvent have a problem of the residual organic solvent, and those produced by hydrolytic extraction (enzyme treatment) are not preferred from the viewpoint of blending with cosmetics or skin external preparations, which are used for the skin for a long period, since the extracts are eventually produced by treatment with a cetylpyridinium chloride solution or ethanol. Further, the tyrosinase-inhibiting activity of earthworm extracts obtained by the method described in Patent Document 3 is still not satisfactory.

Thus, the present invention aims to provide a method for producing a tyrosinase inhibitor, which method enables production of a highly safe tyrosinase inhibitor having excellent tyrosinase-inhibiting action, and a cosmetic produced using a tyrosinase inhibitor obtained by the production method.

As a result of intensive study to solve the above problem, the present inventors discovered that an earthworm component obtained by subjecting a live earthworm to a specific treatment and then grinding the resulting product has excellent tyrosinase-inhibiting action, thereby completing the present invention.

Means for Solving the Problems

That is, the method for producing a tyrosinase inhibitor of the present invention comprises the steps of contacting a live earthworm with hydroxycarboxylic acid powder, diluting the resulting mixture with water to adjust the pH to 2 to 5, and then leaving the resulting dilution to stand for 3 to 180 minutes, or contacting a live earthworm with an aqueous solution of hydroxycarboxylic acid having a pH of 2 to 5 and then leaving the resulting mixture to stand for 3 to 180 minutes; followed by washing the live earthworm with water, grinding the washed earthworm, and then freeze-drying the obtained ground product.

The method for producing a tyrosinase inhibitor of the present invention preferably comprises the step of contacting the live earthworm with a chloride(s) of at least one metal selected from the group consisting of potassium, sodium, magnesium and calcium, which step is carried out before the contacting of the live earthworm with the hydroxycarboxylic acid powder or aqueous solution of hydroxycarboxylic acid.

Further, the method for producing a tyrosinase inhibitor of the present invention preferably comprises the step of leaving the live earthworm to stand in a bright place for 10 to 50 hours and then peeling off dirt attached to the body surface, which step is carried out before the contacting of the live earthworm with the hydroxycarboxylic acid powder or aqueous solution of hydroxycarboxylic acid.

In the method for producing a tyrosinase inhibitor of the present invention, the freeze-drying is preferably carried out by freezing the ground product at −18° C. to −35° C. for 20 to 240 hours and then freeze-drying the resulting product under vacuum.

The method for producing a tyrosinase inhibitor of the present invention preferably further comprises the step of dissolving the freeze-dried ground product in water or an aqueous solution of ethanol and then removing or separating the insoluble fraction.

The cosmetic of the present invention is produced using a tyrosinase inhibitor obtained by any one of the above methods for producing a tyrosinase inhibitor.

Effect of the Invention

The present invention can provide a method for producing a tyrosinase inhibitor without use of an organic solvent or the like, which method enables to obtain a highly safe tyrosinase inhibitor having excellent tyrosinase-inhibiting action.

BRIEF DESCRIPTION OF THE DRAWINGS

FIG. 1 is a graph diagram showing the results of Examples 1 and 2.
FIG. 2 is a graph diagram showing the results of Example 6.
FIG. 3 is a graph diagram showing the results of Example 7.
FIG. 4 is a graph diagram showing the results of Example 8.

BEST MODE FOR CARRYING OUT THE INVENTION

Figure 5:
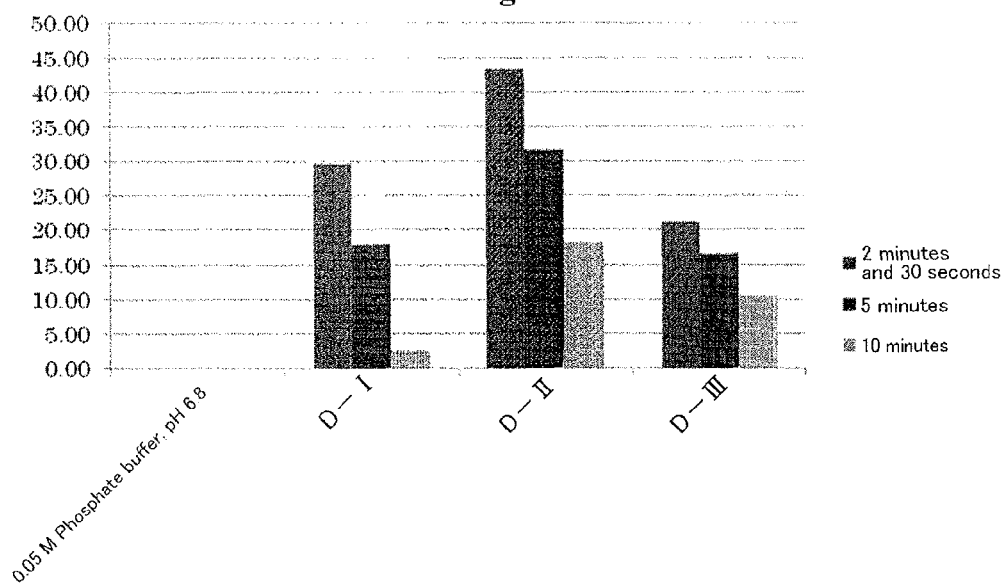
FIG. 5 is a graph diagram showing the results of Example 9.

The method for producing a tyrosinase inhibitor of the present invention comprises the steps of contacting a live earthworm with hydroxycarboxylic acid powder, diluting the resulting mixture with water to adjust the pH to 2 to 5, and then leaving the resulting dilution to stand for 3 to 180 minutes, or contacting a live earthworm with an aqueous solution of hydroxycarboxylic acid having a pH of 2 to 5 and then leaving the resulting mixture to stand for 3 to 180 minutes; followed by washing the live earthworm with water, grinding the washed earthworm, and then freeze-drying the obtained ground product.

Further, the method for producing a tyrosinase inhibitor of the present invention preferably comprises the steps of contacting a live earthworm with the chloride(s) of at least one metal selected from the group consisting of potassium, sodium, magnesium and calcium; and then contacting the live earthworm with hydroxycarboxylic acid powder, diluting the resulting mixture with water to adjust the pH to 2 to 5 and then leaving the resulting dilution to stand for 3 to 180 minutes, or contacting a live earthworm with an aqueous solution of hydroxycarboxylic acid having a pH of 2 to 5 and then leaving the resulting mixture to stand for 3 to 180 minutes; followed by washing the live earthworm with water, grinding the washed earthworm, and then freeze-drying the obtained ground product.

The method for producing a tyrosinase inhibitor of the present invention is a production method that can provide a highly safe tyrosinase inhibitor having excellent tyrosinase-inhibiting action using a live earthworm.

In the production method of the present invention, prior to the treatment of placing live earthworms in an uncomfortable environment, that is, prior to the contacting of live earthworms with a metal chloride(s) or hydroxycarboxylic acid(s), the live earthworms are preferably transferred into a flat container such as a bread container and left to stand in a bright place for 10 to 50 hours, followed by removing dirt attached to the body surface. The length of time during which the earthworms are left to stand in a bright place is more preferably 12 to 24 hours. In terms of the amount of earthworms stored at this time, the earthworms are preferably piled up to attain a thickness of about 30 to 60 mm, preferably about 40 to 50 mm. This flat container is kept free from foreign substances such as sand and mud, and the inside of the container is preferably kept bright at night by light cultivation or the like since earthworms are nocturnal and their daily activity becomes active in a dark place, which may lead to physical exhaustion. By this procedure, the live earthworms exert their self-protective instinct and excrete digests remaining in the digestive tract, with which their whole bodies are covered to prevent evaporation of moisture and thereby to maintain their living environment. Therefore, by repeating peeling off this covering dirt, that is, excrement, by an appropriate method, digests in the digestive tract and dirt attached to the body surface can be finally removed.

The dirt attached to the body surface of earthworms can be peeled off by, for example, covering the live earthworms with a non-woven fabric to allow adsorption of the dirt thereto. By combining this leaving of the earthworms to stand in a bright place followed by removal of dirt attached to the body surface and contacting of the earthworms with a metal chloride(s) and/or a hydroxycarboxylic acid(s), further excretion and removal of toxic substances in the bodies of the earthworms can be expected.

The metal chloride(s) used in another method for producing a tyrosinase inhibitor of the present invention is/are the chloride(s) of at least one metal selected from the group consisting of potassium, sodium, magnesium and calcium. That is, the metal chloride(s) is/are at least one selected from the group consisting of potassium chloride, sodium chloride, magnesium chloride and calcium chloride. Further, the metal chloride(s) may be a mixture of two or more of these, or may be a mixture of one or more of these and one or more harmless components which can be added to food. Examples of such a mixture include dietary salts, rock salts and bay salts. The above-described metal chloride(s) may be used by sprinkling its/their powder on live earthworms, and this causes contact of the earthworms with the metal chloride(s).

In another method for producing a tyrosinase inhibitor of the present invention, it is preferable that live earthworms are brought into contact with a hydroxycarboxylic acid(s) after bringing the live earthworms into contact with a metal chloride(s). Alternatively, the method for producing a tyrosinase inhibitor of the present invention may be carried out by bringing live earthworms into contact with a hydroxycarboxylic acid(s) without bringing the live earthworms into contact with a metal chloride(s).

The contacting with the hydroxycarboxylic acid(s) may also be carried out by sprinkling powder of the hydroxycarboxylic acid(s) on the live earthworms. Alternatively, the live earthworms may be immersed in an aqueous solution of hydroxycarboxylic acid having a pH of 2 to 5. In cases where the contacting with the hydroxycarboxylic acid(s) is carried out after the contacting with the metal chloride(s), the contacting with the hydroxycarboxylic acid(s) is carried out immediately after the contacting with the above-described metal chloride(s). Further, before bringing the live earthworms into contact with a hydroxycarboxylic acid(s), the earthworms are preferably washed with water. Removing the metal chloride(s) by washing with water followed by bringing the live earthworms into contact with the hydroxycarboxylic acid(s) enables production of dry earthworm powder having high enzymatic activities. In cases where the earthworms are washed with water before being brought into contact with the hydroxycarboxylic acid(s), the washing of earthworms with water is carried out preferably within 30 minutes, more preferably within 20 minutes, after the beginning of contacting with the metal chloride(s). The method of washing with water is not restricted, and a known method may be employed.

In cases where live earthworms are kept in contact with powder of a hydroxycarboxylic acid(s) for a long time, their vital functions are lost, and digests in the digestive tract are not excreted. Therefore, the hydroxycarboxylic acid(s) need(s) to be diluted with water as soon as possible, preferably within 30 seconds, more preferably within 20 seconds, to adjust the pH to 2 to 5.

Since the hydroxycarboxylic acid(s) form(s) a living environment uncomfortable to earthworms, the live earthworms try to improve the living environment by excretion of their body fluids and excrement due to their self-protective instinct. Further, since hydroxycarboxylic acids have bactericidal properties, they are expected to play a role not only in promotion of excretion of digests and the like remaining in the digestive tract as described above, but also in killing bacteria attached to the earthworms.

The crystalline hydroxycarboxylic acid used in the method of the present invention is not restricted by the numbers of its hydroxy groups and carboxyl groups, as long as the hydroxycarboxylic acid is in the form of a crystalline body under the conditions of its use. That is, the crystalline hydroxycarboxylic acid may be any of a monohydroxy monocarboxylic acid, monohydroxy polycarboxylic acid, polyhydroxy monocarboxylic acid and polyhydroxy polycarboxylic acid.

Examples of the hydroxycarboxylic acid(s) used in the present invention include glycolic acid, lactic acid, acetic acid, β-hydroxypropionic acid, α-hydroxy-n-butyric acid, β-hydroxy-n-butyric acid, α-hydroxy-n-valeric acid, β-hydroxy-n-valeric acid, malic acid, α-methylmalic acid, α-hydroxyglutaric acid, β-hydroxyglutaric acid, citric acid, malonic acid and succinic acid. Among these, lactic acid, acetic acid, malic acid, citric acid, malonic acid and succinic acid are preferred in view of the fact that these may be used in food and can be easily obtained. A single type of hydroxycarboxylic acid may be used alone, or a mixture of two or more types thereof may be used.

Water accounts for 65% of the total components of tissues of a live earthworm. Although the protective functions of a live earthworm are effective for a certain length of time, death of the live earthworm allows enzymes to act, so that the length of time during which the live earthworm is placed in an uncomfortable environment needs to be carefully controlled. The length of time varies depending on the conditions, and is usually within the range of 3 to 180 minutes.

In the present invention, the live earthworms processed with a hydroxycarboxylic acid(s) are washed with water and then ground into a ground product in the form of a liquid or a paste. The washing is preferably carried out with pure water. The method of washing is not restricted, and a known method for washing with water can be employed. Further, the total length of time spent for the steps before the grinding, that is, the total length of time spent for the steps from sprinkling of a metal chloride(s) on live earthworms to completion of washing out of a hydroxycarboxylic acid(s) with water, is preferably not more than 240 minutes.

The method of above-described grinding is not restricted, and, for example, the grinding is carried out using a homogenizer, blender, homomixer, grinder, French press or the like, usually at 1 to 25° C. In view of suppression of degradation of constituting components of earthworms, the grinding is preferably carried out at a low temperature, preferably at a temperature of 2 to 15° C.

The ground product obtained by grinding earthworms is placed on a stainless-steel tray and subjected to freeze-drying. Although enzymes contained in the living body of the earthworm do not act on live cells, they act on dead cells instantly. Therefore, in the above process, there is a risk of generation of septic gases. In order to prevent the generation of septic gases, the ground product is preferably momentarily subjected to freezing by rapid cooling to −18° C. to −35° C. to suppress the actions of enzymes, followed by freeze-drying.

Thus, pulverization of earthworms without loss of pharmacological actions needs rapid freezing, but, on the other hand, too rapid freezing is not preferred since, in cases where earthworms are frozen too rapidly, impurities present together with proteins, which are major components of the earthworm paste, may form unfrozen spots and cannot be separated. Therefore, the freezing is carried out preferably at a low temperature of −18° C. to −35° C. for 20 to 240 hours, more preferably 50 to 170 hours.

It is important for the freeze-drying to select conditions under which impurities can be removed without remaining together with water. Therefore, the freeze-drying is preferably carried out under control at a pressure of not more than 50 Pa at a temperature of −60° C. to +90° C. while the temperature is increased in a stepwise manner for 10 to 60 hours.

Examples of the method of freeze-drying include a method wherein the ground product is frozen as described above at a temperature of −18° C. to −35° C. for 20 to 240 hours, and the temperature is then increased in several steps within the range of −60° C. to +90° C. and the pressure is decreased in several steps within the range of 25 to 40 Pa, while freeze-drying the product under vacuum for 10 to 60 hours, thereby obtaining sterile pale yellow dry earthworm powder.

The method for producing a tyrosinase inhibitor of the present invention preferably further comprises the step of dissolving the freeze-dried ground product in water or an aqueous solution of ethanol and then removing or separating the insoluble fraction. The process of removing or separating the insoluble fraction can be carried out by precipitation by leaving the solution to stand in the same manner as described above, or by centrifugation, filtration or the like. The process of dissolving the freeze-dried ground product in water or an aqueous solution of ethanol is preferably carried out with stirring or shaking. The length of time required for dissolution of the product in water is preferably 1 to 120 minutes, more preferably 5 to 80 minutes. The ethanol concentration in the aqueous solution of ethanol is not limited, and preferably 10 to 70% (v/v), more preferably 30 to 60%

The form of the tyrosinase inhibitor obtained by the production method of the present invention is not limited. That is, the supernatant obtained after dissolution in water or an aqueous solution of ethanol as described above may be used as it is in the state of an aqueous solution, or may be used after evaporating water to provide a concentrate, or may be used after drying into the form of a powder. The powder obtained by drying the supernatant may be used after dissolving it in water. Alternatively, the powder obtained by freeze-drying of an earthworm paste may be used as it is without dissolution in water or an aqueous solution of ethanol.

The earthworm used as a raw material in the method of the present invention is not limited, and examples of the earthworm include *Lumbricus rubellus, Lumbricus terrestris, Eisenia foetida, Allolobophora caliginosa, Dendrobaena octaedra, Allolobophora japonica* Michaelsen, *Drawida hattamimizu* Hatai, *Pheretima divergens* Michaelsen, *Pheretima communissima, Pheretima agrestis, Pheretima sieboldi* Horst, *Pheretima hilgendorfi, Pontodrilus matsushimensis* Iizuka, *Tubifex hattai* Nomura and *Limnodrilus gotoi* Hatai=*L. Socialis* Stephenson].

The cosmetic of the present invention comprises a tyrosinase inhibitor obtained by the method for producing a tyrosinase inhibitor of the present invention. By the action of the tyrosinase inhibitor, production of melanin can be suppressed, and the effect of producing beautiful skin and the effect of prevention of pigmentation can be expected.

The form of the cosmetic of the present invention is not limited. Depending on the actions and effects of the effective components of the tyrosinase inhibitor, the tyrosinase inhibitor can be applied to any cosmetics for which each action/effect can be utilized. By blending the effective component(s) of the present invention in bases for various cosmetics, the effective component(s) can be applied to forms such as various basic skin care products including creams, skin milks, skin lotions, packs and facial cleansers; various makeup products including foundations, lipsticks, blushers and face powders; various hair cosmetics including hair washes, hair tonics, shampoos and hair conditioners; soaps; manicures; colognes; lotions; emulsions; ointments; sols; gels; powders; sprays; and solids.

The content of the tyrosinase inhibitor of the present invention in each cosmetic is not limited since it may be changed depending on, for example, the mode of the cosmetic and the form of use of the cosmetic. The tyrosinase inhibitor may be contained basically in an effective amount, and, in general, the content of tyrosinase inhibitor in the composition of a cosmetic is 0.0001 to 100% by mass, preferably 0.01 to 10% by mass in terms of the dry weight.

Further, the tyrosinase inhibitor may be blended with additives generally used for cosmetics, and/or other effective components. Examples of the additives and effective components include water, ethanol, oily components, humectants, thickeners, antiseptics, emulsifiers, pharmacologically active components, powders, ultraviolet absorbers, perfumes and emulsion stabilizers.

EXAMPLES

The present invention is described below in more detail by way of Examples. The present invention is not restricted at all by the Examples below.

Preparation of Dry Earthworm Powder

Example 1

After leaving 30 kg of live *Lumbricus rubellus* to stand in a bright place for 24 hours, dirt attached to the body surface was peeled off, followed by spreading the earthworms at a thickness of about 5 cm on a flat dish and sprinkling 250 g of citric acid thereon. The resultant was diluted 15 seconds later by addition of 30 liters of pure water.

When the citric acid powder was sprinkled, the earthworms released a yellow body fluid at once. After the dilution with water, the earthworms were left to stand in this state for 20 minutes.

Subsequently, the live earthworms were removed from the dirty aqueous citric acid solution and washed with water, followed by being ground with a homogenizer at 10° C., to prepare an earthworm paste. Thereafter, this earthworm paste was degassed by aspiration to remove the gas contained therein, and transferred onto a stainless-steel tray, followed by being momentarily and rapidly cooled to −35° C., at which temperature the earthworm paste was kept for 50 hours to allow slow freezing.

The frozen earthworm paste was kept at −35° C. at a pressure of 0 Pa for 2 hours, and the temperature was then increased to 25° C., followed by drying the paste at 40 Pa for 10 hours; at 40° C. at a pressure of 35 Pa for 14 hours; at 65° C. at a pressure of 35 Pa for 12 hours; and finally at a temperature of 80° C. at a pressure of 25 Pa for 6 hours, thereby performing vacuum freeze-drying. By this treatment, a pale yellow dry earthworm powder having a moisture content of 8% by mass was obtained.

Example 2

After leaving 30 kg of live *Lumbricus rubellus* to stand in a bright place for 24 hours, dirt attached to the body surface was peeled off, followed by spreading the earthworms on a flat dish at a thickness of about 5 cm and sprinkling 250 g of sodium chloride uniformly thereon. The earthworms were washed 20 minutes later with water.

Subsequently, 250 g of citric acid was sprinkled on the earthworms in a similar manner, and the resultant was diluted 15 seconds later by adding 30 liters of pure water. At this time, the pH immediately after the addition of water was 2.25, and the pH after the complete dilution was 2.74.

When the citric acid powder was sprinkled, the earthworms released a yellow body fluid at once. After the dilution with water, the earthworms were left to stand in this state for 20 minutes.

Subsequently, the live earthworms were removed from the dirty aqueous citric acid solution and washed with water, followed by being ground with a homogenizer at 10° C., to prepare an earthworm paste. Thereafter, this earthworm paste was degassed by aspiration to remove the gas contained therein, and transferred onto a stainless-steel tray, followed by being momentarily and rapidly cooled to −35° C., at which temperature the earthworm paste was kept for 50 hours to allow slow freezing.

The frozen earthworm paste was kept at −35° C. at a pressure of 0 Pa for 2 hours, and the temperature was then increased to 25° C., followed by drying the paste at 40 Pa for 10 hours; at 40° C. at a pressure of 35 Pa for 14 hours; at 65° C. at a pressure of 35 Pa for 12 hours; and finally at a temperature of 80° C. at a pressure of 25 Pa for 6 hours, thereby performing vacuum freeze-drying. By this treatment, a pale yellow dry earthworm powder having a moisture content of 8% by mass was obtained.

To 1 g of each dry earthworm powder obtained as described above, 20 mL of ion-exchanged water was added, and the resulting mixture was stirred for 1 hour. Thereafter, centrifugation (10000×g, room temperature, 15 minutes) was performed to separate the supernatant, to provide a measurement sample.

[Measurement Reagents]

For measurement of the tyrosinase-inhibiting activity, the following reagents were used.

Phosphate buffer (phosphoric acid+sodium phosphate, 0.05 M, pH 6.8)

Tyrosinase (mushroom-derived, 50 U/mL in phosphate buffer)

L-DOPA (2.5 mM in phosphate buffer)

[Measurement Method]

To 500 μL of phosphate buffer, 200 μL of tyrosinase was added, and the resulting mixture was stirred. Thereafter, 100 μL of the above measurement sample or ion-exchanged water (control) was further added thereto, and the resulting mixture was incubated at 25° C. for 3 minutes. Subsequently, 250 μL, of L-DOPA was added to the mixture, and the resulting mixture was stirred, followed by measurement of the absorbance at 490 nm. After starting the measurement, the absorbance was plotted every 30 seconds during 10 minutes of the measurement. An approximate line between the beginning of measurement and Minute 10 of the measurement was drawn, and the slope of the line was calculated. The ratio of the slope of this approximate line to the slope obtained by the reaction with ion-exchanged water (control) was represented as a graph by defining the latter slope as 100. The graph is shown in FIG. 1.

As is evident from FIG. 1, the tyrosinase inhibitors of the present invention strongly inhibited the tyrosinase function. Tyrosinase has an action to change L-tyrosine to L-DOPA and then to L-dopaquinone. Since melanin pigment is synthesized thereafter from L-dopaquinone via several steps of reactions, inhibition of the tyrosinase activity leads to inhibition of melanin synthesis. Therefore, the tyrosinase inhibitor of the present invention is suitable for uses in cosmetics, especially skin-whitening cosmetics.

Reference Example 1

According to the method described in Japanese Patent Publication No. 2090412, a freeze-dried earthworm powder was obtained.

That is, after leaving 30 kg of live *Lumbricus rubellus* to stand in a bright place for 24 hours, dirt attached to the body surface was peeled off, followed by spreading the earthworms at a thickness of about 5 cm on a flat dish and adding 30 liter of water thereto. Thereafter, the resultant was left to stand in this state for 20 minutes. Subsequently, the live earthworms were removed from water, and washed with water, followed by being ground using a homogenizer at 10° C., to prepare an earthworm paste. Thereafter, this earthworm paste was degassed by aspiration to remove the gas contained therein, and transferred onto a stainless-steel tray, followed by being momentarily and rapidly cooled to −35° C., at which temperature the earthworm paste was kept for 50 hours to allow slow freezing.

The frozen earthworm paste was kept at −35° C. at a pressure of 0 Pa for 2 hours, and the temperature was then increased to 25° C., followed by drying the paste at 40 Pa for 10 hours; at 40° C. at a pressure of 35 Pa for 14 hours; at 65° C. at a pressure of 35 Pa for 12 hours; and finally at a temperature of 80° C. at a pressure of 25 Pa for 6 hours, thereby performing vacuum freeze-drying. By this treatment, a pale yellow dry earthworm powder having a moisture content of 8% by mass was obtained.

The freeze-dried powder was dissolved in 50% aqueous solution of ethanol such that the ratio of ethanol:freeze-dried powder was 20:1 (v/w), and the resulting solution was shaken at room temperature (25° C.) at 1500 rpm for 1 hour. Thereafter, centrifugation was carried out at 4° C. at 10000×g for 15 minutes to separate the supernatant, and the obtained supernatant was concentrated under reduced pressure at 75° C. for 15 minutes, followed by freeze-drying the resulting concentrate to obtain freeze-dried powder A-I.

Reference Example 2

Freeze-dried powder B-I was obtained in the same manner as in the Reference Example 1 described above, except that ion-exchanged water was used instead of 50% aqueous solution of ethanol.

Reference Example 3

Freeze-dried powder C-I was obtained in the same manner as in the Reference Example 1 described above, except that ion-exchanged water was used instead of 50% aqueous solution of ethanol and the final concentration under reduced pressure was not carried out.

Example 3

After washing 30 kg of live *Lumbricus rubellus* with water to remove dirt attached to the skin surface, the earthworms were spread at a thickness of about 5 cm on a flat dish, and 250 g of citric acid was uniformly sprinkled thereon. The resultant was diluted 15 seconds later by addition of 30 liters of pure water.

Subsequently, the earthworms immersed in dilute citric acid were left to stand at 20° C. for 60 minutes. Subsequently, the live earthworms were removed from the dirty aqueous citric acid solution and washed with water, followed by being ground with a homogenizer at 10° C., to prepare an earthworm paste. Thereafter, this earthworm paste was degassed by aspiration to remove the gas contained therein, and transferred onto a stainless-steel tray, followed by being momentarily and rapidly cooled to −30° C., at which temperature the earthworm paste was kept for 50 hours to allow slow freezing.

The thus frozen earthworm paste was kept at −30° C. at a reduced pressure of 5 Pa for 10 hours, and then dried at an increased temperature of 20° C. at a pressure of 10 Pa for 10 hours and subsequently at 40° C. for 10 hours. Finally, the earthworm paste was kept at a temperature of 80° C. at a pressure of 5 Pa for 5 hours to complete vacuum freeze-drying. By this treatment, a pale yellow dry earthworm powder having a moisture content of 8% by mass was obtained.

The freeze-dried powder was dissolved in 50% aqueous solution of ethanol such that the ratio of ethanol:freeze-dried powder became 20:1 (v/w), and the resulting solution was shaken at room temperature (25° C.) at 1500 rpm for 1 hour. Thereafter, centrifugation was carried out at 4° C. at 10000×g for 15 minutes to separate the supernatant, and the obtained supernatant was concentrated under reduced pressure at 75° C. for 15 minutes, followed by freeze-drying the resulting concentrate to obtain freeze-dried powder A-II.

Example 4

Freeze-dried powder B-II was obtained in the same manner as in the Example 3 described above, except that ion-exchanged water was used instead of 50% aqueous solution of ethanol.

Example 5

Freeze-dried powder C-II was obtained in the same manner as in the Example 3 described above, except that ion-exchanged water was used instead of 50% aqueous solution of ethanol and the final concentration under reduced pressure was not carried out.

Example 6

In the same manner as in the Example 2 described above, a pale yellow freeze-dried powder was obtained.

The freeze-dried powder was dissolved in 50% aqueous solution of ethanol such that the ratio of ethanol:freeze-dried powder became 20:1 (v/w), and the resulting solution was shaken at room temperature (25° C.) at 1500 rpm for 1 hour. Thereafter, centrifugation was carried out at 4° C. at 10000×g for 15 minutes to separate the supernatant, and the obtained supernatant was concentrated under reduced pressure at 75° C. for 15 minutes, followed by freeze-drying the resulting concentrate to obtain freeze-dried powder A-III.

Example 7

Freeze-dried powder B-III was obtained in the same manner as in the Example 6 described above, except that ion-exchanged water was used instead of 50% aqueous solution of ethanol.

Example 8

Freeze-dried powder C-III was obtained in the same manner as in the Example 6 described above, except that ion-exchanged water was used instead of 50% aqueous solution of ethanol and the final concentration under reduced pressure was not carried out.

To 0.1 g each of the freeze-dried powders A-I, A-II, A-III, B-I, B-II, B-III, C-I, C-II and C-III, phosphate buffer was added such that the powder was contained therein at 0.05 g/ml. The resulting solution was shaken (1500 rpm, 25° C., 1 hour), and then centrifuged (10000×g, 4° C., 15 minutes), to collect the supernatant as a measurement sample.

Tyrosinase (Sigma-Aldrich Co., derived from mushroom) and L-DOPA (NACALAI TESQE, INC.) solutions were prepared with phosphate buffer such that a predetermined concentration (2.5 mM) was attained. The mixture of 0.5 ml of phosphate buffer, 0.2 ml of tyrosinase (250 U/ml) and 0.1 ml of the measurement sample was incubated using a spectrophotometer at 37° C. for 3 minutes. Measurement was started 2 minutes and 48 seconds after the beginning of incubation, and 0.25 ml of L-DOPA (2.5 mM) was added to the mixture at Minute 3, followed by incubating the resulting mixture at 37° C. for 10 minutes while measuring the absorbance at 490 nm (every 10 seconds).

From the measurement results, the tyrosinase activity inhibition ratio (%) defined by the equations below was calculated (the equations below show the case of the value measured at Minute 5).

At: The increase in the absorbance of the measurement solution containing tyrosinase and L-DOPA during the period between 30 seconds after the beginning of measurement and 5 minutes and 30 seconds after the beginning of measurement.

Ac: The increase in the absorbance of the measurement solution that contains tyrosinase but does not contain L-DOPA during the period between 30 seconds after the beginning of measurement and 5 minutes and 30 seconds after the beginning of measurement.

At0: The increase in the absorbance of the measurement solution that does not contain tyrosinase but contains L-DOPA during the period between 30 seconds after the beginning of measurement and 5 minutes and 30 seconds after the beginning of measurement.

Ac0: The increase in the absorbance of the measurement solution containing neither tyrosinase nor L-DOPA during the period between 30 seconds after the beginning of measurement and 5 minutes and 30 seconds after the beginning of measurement.

$$\text{Activity ratio (\%)} = ([At]-[At0])/([Ac]-[Ac0]) \times 100$$

$$\text{Tyrosinase activity inhibition ratio (\%)} = 100 - \text{activity ratio}$$

The results are shown below in Table 1 to Table 3 and FIG. 2 to FIG. 4. In each table, "0.05 M phosphate buffer, pH 6.8" corresponds to the control prepared using phosphate buffer instead of the measurement sample.

TABLE 1

Tyrosinase activity inhibition ratio (%)

| | Elapsed time | | |
|---|---|---|---|
| | 2 minutes and 30 seconds | 5 minutes | 10 minutes |
| 0.05M Phosphate buffer, pH 6.8 | 0.00 | 0.00 | 0.00 |
| A-I | 25.16 | 17.98 | 10.74 |
| A-II | 22.44 | 17.67 | 12.10 |
| A-III | 57.85 | 44.64 | 27.88 |

TABLE 2

Tyrosinase activity inhibition ratio (%)

| | Elapsed time | | |
|---|---|---|---|
| | 2 minutes and 30 seconds | 5 minutes | 10 minutes |
| 0.05M Phosphate buffer, pH 6.8 | 0.00 | 0.00 | 0.00 |
| B-I | 19.74 | 8.78 | 0.00 |
| B-II | 16.28 | 7.84 | 0.00 |
| B-III | 45.56 | 30.09 | 10.82 |

TABLE 3

Tyrosinase activity inhibition ratio (%)

| | Elapsed time | | |
|---|---|---|---|
| | 2 minutes and 30 seconds | 5 minutes | 10 minutes |
| 0.05M Phosphate buffer, pH 6.8 | 0.00 | 0.00 | 0.00 |
| C-I | 25.00 | 12.95 | 0.00 |
| C-II | 25.74 | 13.61 | 0.00 |
| C-III | 53.25 | 37.43 | 16.92 |

As is evident from the Tables 1 to 3 shown above and FIGS. 2 to 4, the tyrosinase inhibitors composed of freeze-dried earthworm powder obtained by the production method of the present invention showed an inhibition activity against tyrosinase. The inhibitors obtained by the methods comprising the step of bringing live earthworms before grinding treatment into contact with a metal salt and a hydroxycarboxylic acid had especially high tyrosinase inhibition activities.

Comparative Example 1

According to the method described in Japanese Unexamined Patent Application Publication No. S63-238009, live earthworms (90.0 g) were warmed in hot water at about 80° C. for 20 minutes, and washed with tap water. After draining, the earthworms were processed using a mixer to obtain an earthworm paste.

The paste was dissolved in 50% aqueous solution of ethanol such that the ratio of ethanol:paste became 10:1 (v/w), and the resultant was kept at a low temperature of 5 to 10° C. with stirring for 2 weeks. Thereafter, centrifugation was performed at 4° C. at 10000×g for 15 minutes. The supernatant was separated and then concentrated under reduced pressure at 75° C. for 15 minutes, followed by freeze-drying the resulting concentrate to obtain freeze-dried powder D-I.

Example 9

In the same manner as in the Example 2 described above, a pale yellow freeze-dried powder was obtained.

The freeze-dried powder was dissolved in 50% aqueous solution of ethanol such that the ratio of ethanol:freeze-dried powder became 10:1 (v/w), and the resultant was kept at a low temperature of 5 to 10° C. with stirring for 2 weeks. Thereafter, centrifugation was performed at 4° C. at 10000×g for 15 minutes. The supernatant was separated and then concentrated under reduced pressure at 75° C. for 15 minutes, followed by freeze-drying the resulting concentrate to obtain freeze-dried powder D-II.

Reference Example 4

In the same manner as in Reference Example 1, a freeze-dried earthworm powder was obtained according to the method described in Japanese Patent Publication No. 2090412.

The freeze-dried powder was dissolved in 50% aqueous solution of ethanol such that the ratio of ethanol:freeze-dried powder became 10:1 (v/w), and the resultant was kept at a low temperature of 5 to 10° C. with stirring for 2 weeks. Thereafter, centrifugation was performed at 4° C. at 10000×g for 15 minutes. The supernatant was separated and then concentrated under reduced pressure at 75° C. for 15 minutes, followed by freeze-drying the resulting concentrate to obtain freeze-dried powder D-III.

To 0.1 g each of the freeze-dried powders D-I, D-II and D-III, phosphate buffer was added such that the powder was contained therein at 0.05 g/ml. The resulting solution was shaken (1500 rpm, 25° C., 1 hour), and then centrifuged (10000×g, 4° C., 15 minutes), to collect the supernatant as a measurement sample.

Tyrosinase (Sigma-Aldrich Co., derived from mushroom) and L-DOPA (NACALAI TESQE, INC.) solutions were prepared with phosphate buffer such that a predetermined concentration (2.5 mM) was attained. The mixture of 0.5 ml of phosphate buffer, 0.2 ml of tyrosinase (250 U/ml) and 0.1 ml of the measurement sample was incubated using a spectrophotometer at 37° C. for 3 minutes. Measurement was started 2 minutes and 48 seconds after the beginning of incubation, and 0.25 ml of L-DOPA (2.5 mM) was added to the mixture at Minute 3, followed by incubating the resulting mixture at 37° C. for 10 minutes while measuring the absorbance at 490 nm (every 10 seconds).

From the measurement results, the tyrosinase activity inhibition ratio (%) defined by the equations below was calculated (the equations below show the case of the value measured at Minute 5).

At: The increase in the absorbance of the measurement solution containing tyrosinase and L-DOPA during the period between 30 seconds after the beginning of measurement and 5 minutes and 30 seconds after the beginning of measurement.

Ac: The increase in the absorbance of the measurement solution that contains tyrosinase but does not contain L-DOPA during the period between 30 seconds after the beginning of measurement and 5 minutes and 30 seconds after the beginning of measurement.

At0: The increase in the absorbance of the measurement solution that does not contain tyrosinase but contains L-DOPA during the period between 30 seconds after the beginning of measurement and 5 minutes and 30 seconds after the beginning of measurement.

Ac0: The increase in the absorbance of the measurement solution containing neither tyrosinase nor L-DOPA during the period between 30 seconds after the beginning of measurement and 5 minutes and 30 seconds after the beginning of measurement.

$$\text{Activity ratio (\%)} = ([At]-[At0])/([Ac]-[Ac0]) \times 100$$

$$\text{Tyrosinase activity inhibition ratio (\%)} = 100 - \text{activity ratio}$$

The results are shown below in Table 4 and FIG. 5. In each table, "0.05 M phosphate buffer, pH 6.8" corresponds to the control prepared using phosphate buffer instead of the measurement sample.

TABLE 4

| | Tyrosinase activity inhibition ratio (%) | | |
|---|---|---|---|
| | Elapsed time | | |
| | 2 minutes and 30 seconds | 5 minutes | 10 minutes |
| 0.05M Phosphate buffer, pH 6.8 | 0.00 | 0.00 | 0.00 |
| D-I | 29.73 | 18.00 | 2.46 |
| D-II | 43.37 | 31.76 | 18.24 |
| D-III | 21.21 | 16.67 | 10.59 |

As is evident from the Table 4 shown above and FIG. 5, the tyrosinase inhibitors composed of freeze-dried earthworm powder obtained by the production method of the present invention, especially by the method comprising the step of bringing live earthworms before grinding treatment into contact with a metal salt and a hydroxycarboxylic acid (D-II), had higher tyrosinase inhibition activities than the tyrosinase inhibitor obtained by the production method according to the method described in Japanese Unexamined Patent Application Publication No. S63-238009 (D-I).

Comparative Example 2

According to the method described in Japanese Unexamined Patent Application Publication No. S63-238009, live earthworms (90.0 g) were warmed in hot water at about 80° C. for 20 minutes, and washed with tap water. After draining, the earthworms were processed using a mixer to obtain an earthworm paste.

The paste was dissolved in ion-exchanged water such that the ratio of ion-exchanged water:paste became 10:1 (v/w), followed by addition of chloroform thereto in an amount of 50% with respect to the ion-exchanged water added. The resulting mixture was shaken and then left to stand at a low temperature of 5 to 10° C. for 24 hours. The aqueous layer was then removed, and 50% aqueous solution of ethanol in an amount of 90% with respect to the amount of the aqueous layer was added thereto. The resulting mixture was stirred and left to stand at a low temperature of 5 to 10° C. for 24 hours. Thereafter, centrifugation was performed at 4° C. at 10000×g for 15 minutes. The precipitate layer was separated and freeze-dried to obtain freeze-dried powder E-I. On the other hand, the supernatant was concentrated under reduced pressure at 75° C. for 15 minutes, followed by freeze-drying the resulting concentrate to obtain freeze-dried powder F-I.

Example 10

Using 90.0 g of live earthworms, a pale yellow freeze-dried powder was obtained in the same manner as in the Example 2 described above.

The freeze-dried powder was dissolved in ion-exchanged water such that the ratio of ion-exchanged water:freeze-dried powder became 10:1 (v/w), followed by addition of chloroform thereto in an amount of 50% with respect to the ion-exchanged water added. The resulting mixture was shaken and then left to stand at a low temperature of 5 to 10° C. for 24 hours. The aqueous layer was then removed, and 50% aqueous solution of ethanol in an amount of 90% with respect to the amount of the aqueous layer was added thereto. The resulting mixture was stirred and left to stand at a low temperature of 5 to 10° C. for 24 hours. Thereafter, centrifugation was performed at 4° C. at 10000×g for 15 minutes. The precipitate layer was separated and freeze-dried to obtain freeze-dried powder E-II. On the other hand, the supernatant was concentrated under reduced pressure at 75° C. for 15 minutes, followed by freeze-drying the resulting concentrate to obtain freeze-dried powder F-II.

Reference Example 5

In the same manner as in Reference Example 1, a freeze-dried earthworm powder was obtained according to the method described in Japanese Patent Publication No. 2090412.

The freeze-dried powder was dissolved in ion-exchanged water such that the ratio of ion-exchanged water:freeze-dried powder became 10:1 (v/w), followed by addition of chloroform thereto in an amount of 50% with respect to the ion-exchanged water added. The resulting mixture was shaken and then left to stand at a low temperature of 5 to 10° C. for 24 hours. The aqueous layer was then removed, and 50% aqueous solution of ethanol in an amount of 90% with respect to the amount of the aqueous layer was added thereto. The resulting mixture was stirred and left to stand at a low temperature of 5 to 10° C. for 24 hours. Thereafter, centrifugation was performed at 4° C. at 10000×g for 15 minutes. The precipitate layer was separated and freeze-dried to obtain freeze-dried powder E-III. On the other hand, the supernatant was concentrated under reduced pressure at 75° C. for 15 minutes, followed by freeze-drying the resulting concentrate to obtain freeze-dried powder F-III.

To 0.1 g each of the freeze-dried powders E-I, E-II, E-III, F-I, F-II and F-III, phosphate buffer was added such that the powder was contained therein at 0.05 g/ml. The resulting solution was shaken (1500 rpm, 25° C., 1 hour), and then centrifuged (10000×g, 4° C., 15 minutes), to collect the supernatant as a measurement sample.

Tyrosinase (Sigma-Aldrich Co., derived from mushroom) and L-DOPA (NACALAI TESQE, INC.) solutions were prepared with phosphate buffer such that a predetermined concentration (2.5 mM) was attained. The mixture of 0.5 ml of phosphate buffer, 0.2 ml of tyrosinase (250 U/ml) and 0.1 ml of the measurement sample was incubated using a spectrophotometer at 37° C. for 3 minutes. Measurement was started 2 minutes and 48 seconds after the beginning of incubation, and 0.25 ml of L-DOPA (2.5 mM) was added to the mixture at Minute 3, followed by incubating the resulting mixture at 37° C. for 10 minutes while measuring the absorbance at 490 nm (every 10 seconds).

From the measurement results, the tyrosinase activity inhibition ratio (%) defined by the equations below was calculated (the equations below show the case of the value measured at Minute 5).

At: The increase in the absorbance of the measurement solution containing tyrosinase and L-DOPA during the period between 30 seconds after the beginning of measurement and 5 minutes and 30 seconds after the beginning of measurement.

Ac: The increase in the absorbance of the measurement solution that contains tyrosinase but does not contain L-DOPA during the period between 30 seconds after the beginning of measurement and 5 minutes and 30 seconds after the beginning of measurement.

At0: The increase in the absorbance of the measurement solution that does not contain tyrosinase but contains L-DOPA during the period between 30 seconds after the beginning of measurement and 5 minutes and 30 seconds after the beginning of measurement.

Ac0: The increase in the absorbance of the measurement solution containing neither tyrosinase nor L-DOPA during the period between 30 seconds after the beginning of measurement and 5 minutes and 30 seconds after the beginning of measurement.

Activity ratio (%)=([At]−[At0])/([Ac]−[Ac0])×100

Tyrosinase activity inhibition ratio (%)=100−activity ratio

Figure 6:
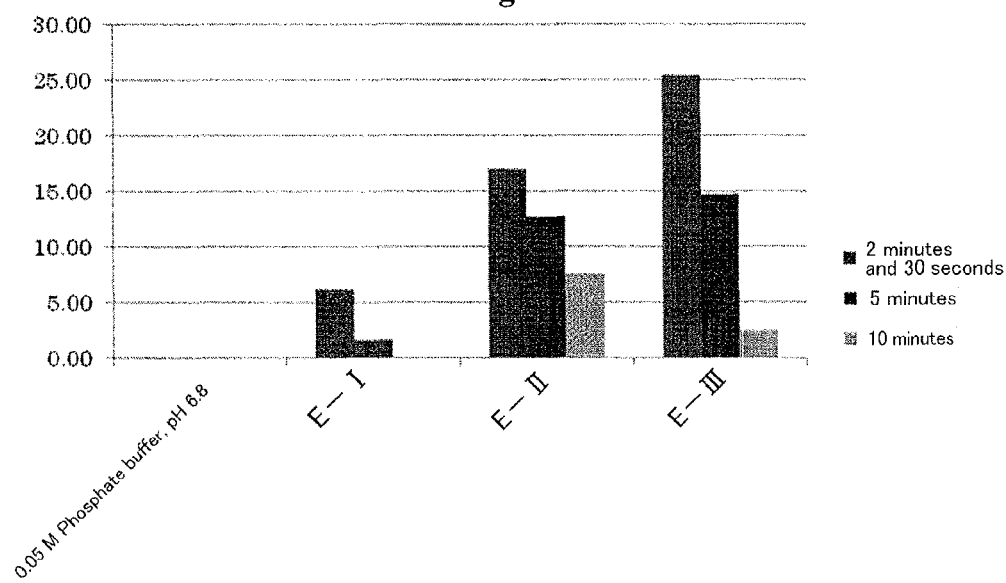
FIG. 6 is a graph diagram showing the results of Example 10.
Figure 7:
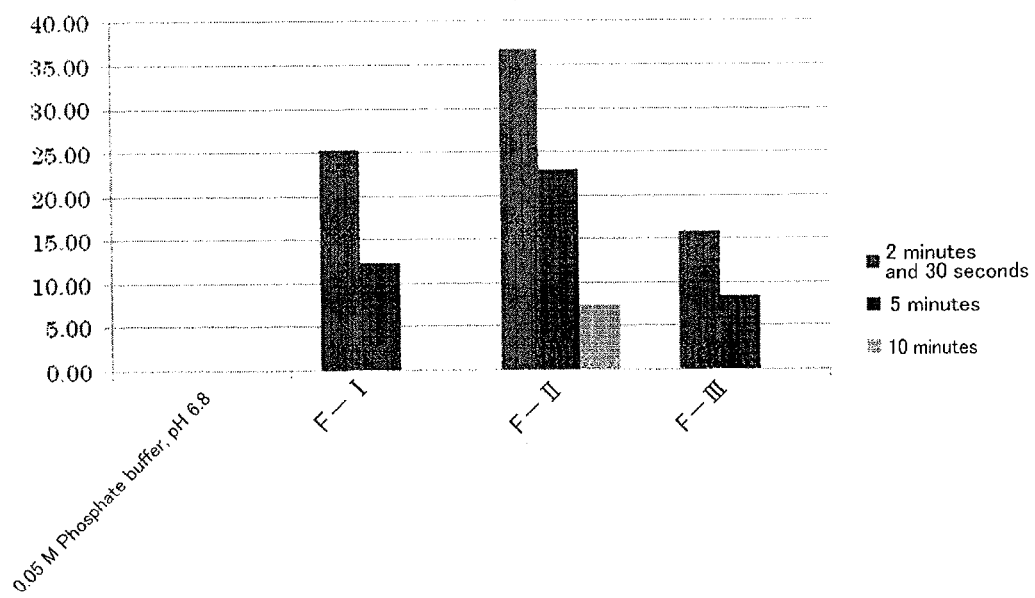
FIG. 7 is a graph diagram showing the results of Example 10.

The results are shown below in Tables 5 and 6 and FIGS. 6 and 7. In each table, "0.05 M phosphate buffer, pH 6.8" corresponds to the control prepared using phosphate buffer instead of the measurement sample.

TABLE 5

| Tyrosinase activity inhibition ratio (%) | | | |
|---|---|---|---|
| | Elapsed time | | |
| | 2 minutes and 30 seconds | 5 minutes | 10 minutes |
| 0.05M Phosphate buffer, pH 6.8 | 0.00 | 0.00 | 0.00 |
| E-I | 6.18 | 1.62 | 0.00 |
| E-II | 16.99 | 12.69 | 7.64 |
| E-III | 25.48 | 14.80 | 2.45 |

TABLE 6

| Tyrosinase activity inhibition ratio (%) | | | |
|---|---|---|---|
| | Elapsed time | | |
| | 2 minutes and 30 seconds | 5 minutes | 10 minutes |
| 0.05M Phosphate buffer, pH 6.8 | 0.00 | 0.00 | 0.00 |
| F-I | 25.34 | 12.31 | 0.00 |
| F-II | 36.74 | 22.99 | 7.29 |
| F-III | 15.91 | 8.54 | 0.00 |

As is evident from the Tables 5 and 6 shown above and FIGS. 6 and 7, the tyrosinase inhibitors composed of freeze-dried earthworm powder obtained by the production method of the present invention, especially by the method comprising the step of bringing live earthworms before grinding treatment into contact with a metal salt and a hydroxycarboxylic acid (E-II, F-II), had higher tyrosinase inhibition activities than the tyrosinase inhibitors obtained by the production method according to the method described in Japanese Unexamined Patent Application Publication No. S63-238009 (E-I, F-I).

The invention claimed is:

1. A method for producing a tyrosinase inhibitor, comprising the steps of:
    contacting a live earthworm with a chloride(s) of at least one metal selected from the group consisting of potassium, sodium, magnesium and calcium; followed by
    contacting the live earthworm with hydroxycarboxylic acid powder, diluting the resulting mixture with water to adjust the pH to 2 to 5 and then leaving the resulting dilution to stand for 3 to 180 minutes, or contacting the live earthworm with an aqueous solution of hydroxycarboxylic acid having a pH of 2 to 5 and then leaving the resulting mixture to stand for 3 to 180 minutes; followed by
    washing the live earthworm with water, grinding the washed earthworm, and then freeze-drying the obtained ground product,
    wherein the step of contacting a live earthworm with a chloride(s) comprises sprinkling a powder of the chloride(s) on the live earthworm and washing the live earthworm with water within 30 minutes after initial contact of the earthworm with the chloride(s).

2. The method for producing a tyrosinase inhibitor according to claim 1, comprising the step of leaving the live earthworm to stand in a bright place for 10 to 50 hours, peeling off dirt attached to the body surface, and then contacting the live earthworm with said chloride(s) of a metal(s), which step is carried out before the contacting of the live earthworm with said chloride(s).

3. The method for producing a tyrosinase inhibitor according to claim 1, wherein said freeze-drying is carried out by freezing the ground product at −18° C. to −35° C. for 20 to 240 hours and then freeze-drying the resulting product under vacuum.

4. The method for producing a tyrosinase inhibitor according to claim 1, comprising the step of dissolving said freeze-dried ground product in water and then removing or separating a resulting insoluble fraction.

* * * * *